(12) United States Patent
Müller et al.

(10) Patent No.: US 6,239,315 B1
(45) Date of Patent: May 29, 2001

(54) SINGLE-STEP METHOD FOR PRODUCING GLYCOL MONOETHERS FROM OLEFINS

(75) Inventors: Ulrich Müller, Neustadt; Georg Heinrich Grosch, Bad Dürkheim; Andreas Walch, Heidelberg; Norbert Rieber, Mannheim, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/403,590

(22) PCT Filed: Apr. 17, 1998

(86) PCT No.: PCT/EP98/02281

§ 371 Date: Oct. 25, 1999

§ 102(e) Date: Oct. 25, 1999

(87) PCT Pub. No.: WO98/47845

PCT Pub. Date: Oct. 29, 1998

(30) Foreign Application Priority Data

Apr. 24, 1997 (DE) ............................................... 197 17 320

(51) Int. Cl.$^7$ ...................................................... C07C 43/11
(52) U.S. Cl. ............................................. 568/619; 568/618
(58) Field of Search .................................... 568/618, 619; 502/64, 67, 102, 150, 168, 232

(56) References Cited

U.S. PATENT DOCUMENTS 4,476,327 * 10/1984 Neri et al. ............................. 568/678
4,833,260 * 5/1989 Neri et al. ............................. 549/531

FOREIGN PATENT DOCUMENTS

1122800 * 8/1968 (GB) .

* cited by examiner

Primary Examiner—Alan Siegel
(74) Attorney, Agent, or Firm—Oblon, Spivak, McClelland, Maier & Neustadt, P.C.

(57) ABSTRACT

A process for preparing glycol monoethers from olefins comprises reacting the olefins with an epoxidizing reagent in the simultaneous presence of hydroxyl-containing organic compounds over a mixture of epoxidation catalysts and alkoxylation catalysts.

10 Claims, No Drawings

SINGLE-STEP METHOD FOR PRODUCING GLYCOL MONOETHERS FROM OLEFINS

The present invention relates to an improved process for preparing glycol monoethers from olefins. The invention further relates to a catalyst mixture which is used in the process of the present invention.

Glycol monoethers are widely used industrially as solvents, absorption liquids in gas scrubbing, antifreezes, hydraulic fluids, lubricants, plasticizers, surfactants, precursors for fiber products such as polyesters or urethanes, additives for printing inks and in cosmetic and skincare products.

The most important products are the corresponding glycol ethers of ethylene and propene. These glycol ethers are usually prepared by reacting epoxides of the parent olefins with the corresponding alcohols.

A disadvantage of this procedure is that a multi-stage process is required which involves initial preparation of the epoxides from the olefins followed by ring-opening reaction of the epoxides with alcohols at a higher temperature using, for example, sulfuric acid.

It is an object of the present invention to provide a simpler process for preparing glycol monoethers.

We have found that, surprisingly, this object is achieved and the above-described disadvantages are overcome by a simple single-stage synthesis which involves reacting olefins with a conventional epoxidizing reagent over suitable epoxidation catalyts and simultaneously allowing the presence of hydroxyl-containing organic compounds, such as alcohols, and acidic or basic alkoxylation catalysts. The epoxide intermediates are reacted in situ over the added alkoxylation catalysts to give glycol monoethers.

The present invention accordingly provides a process for preparing glycol monoethers from olefins, which comprises reacting the olefins with an epoxidizing reagent in the simultaneous presence of hydroxyl-containing organic compounds over a mixture of epoxidation catalysts and alkoxylation catalysts.

Preferred epoxidation catalysts in the catalyst mixture are titanium-containing silicates or titanium-, vanadium-, germanium- or tin-containing zeolites, in particualr titanium or vanadium silicalites having a zeolite structure assigned by X-ray diffraction to the MFI, MEL, BEA, MTW, TON, PER or MFI/MEL mixed structure. Such epoxidation catalysts are described, for example, in DE-A 44 25 672. According to DE-A 44 25 672, the abovementioned titanium or vanadium silicalites may contain noble metals such as platinum metals in amounts of 0.01–20% by weight, which is particularly advantageous when the epoxidizing reagent used is a hydrogen/oxygen mixture.

Preferred alkoxylation catalysts in the catalyst mixture are acidic catalysts in the form of mineral acids or in the form of solid acidic heterogeneous catalysts, and solid basic catalysts.

Examples of mineral acids are sulfuric acid, hydrochloric acid and orthophosphoric acid; for the purposes of the present invention, mineral acids include sufficiently acidic organic sulfonic acids and carboxylic acids such as p-toluenesulfonic acid, methanesulfonic acid or trifluoroacetic acid.

Solid alkoxylation catalysts are particularly suitable, i.e. those which do not dissolve in the reaction medium and which are present as solid phase (as heterogeneous catalysts) during the reaction.

Preference is given to solid acidic heterogeneous catalysts based on supported mineral acids, polymeric acidic ion exchange resins, composites of acidic ion exchange resins in inorganic materials, acidic metal oxides or acid zeolites. Examples of such heterogeneous catalysts are K10-type acidic sheet silicates, acidic metal oxides as described by Arata in Appl. Catalysis A: General 146 (1996), 3-32, and acidic zeolites of the structure type MFI (for example H-ZSM-5 zeolite), MEL, MFI/MEL, BEA (for example H-B-β-zeolite), MOR, FER, NES, ERI, OFF, MAZ, FAU, TON, CHA, RUT, BOG, LTA, NON, MTN, HEU, AFI, MTW, DOE, EUO, MTT, RHO, CAN, LTL, GIS, GME, VFI, EMT, DDR, SGT, CON, ZON or MFS.

Preference is furthermore given to solid basic catalysts based on alkali metal or alkaline earth metal oxides or hydroxides, supported bases, polymeric basic ion exchange resins, dendrimeric amines, talcites or hydrotalcites.

The above-described catalyst mixture usually comprises from 1 to 99 parts by weight of epoxidation catalysts and from 99 to 1 parts by weight of alkoxylation catalyts, when the latter are present in solid form, i.e. as heterogeneous catalysts. Preferred ranges for the proportions of these two types of catalyst are 5–95 parts by weight/95–5 parts by weight and in particular 20–80 parts by weight: 80–20 parts by weight. The above-described catalyst mixture may additionally comprise further conventional auxiliaries. When free mineral acids are present as alkoxylation catalysts, the proportion of epoxidation catalysts to alkoxylation catalysts is usually 90–99.999 parts by weight: 10–0.001 parts by weight, in particular 99–99.99 parts by weight: 1–0.01 parts by weight.

Since the above-described mixture of the solid epoxidation catalysts and the solid alkoxylation catalysts is novel, the present invention also provides a catalyst mixture for the single-stage epoxidation and alkoxylation of olefins, consisting of from 1 to 99 parts by weight of epoxidation catalysts and from 99 to 1 part by weight of solid alkoxylation catalysts.

Particularly useful epoxidizing reagents for the process of the present invention are aqueous hydrogen peroxide or a hydrogen/oxygen mixture. The use of hydrogen/oxygen mixtures for epoxidation is described, for example, in DE-A 44 25 672. However, organic peracids or hydroperoxides are also useful as epoxidizing reagents.

Hydroxyl-containing organic compounds are in principle any mono- and polyhydroxy compounds having sufficient O—H acidity. Preference is given to linear or branched $C_1$- to $C_{20}$-alkanols, $C_5$- to $C_8$-cycloalkanols and $C_7$- to $C_{20}$-arylalkanols. Examples of such alcohols are methanol, ethanol, propanol, isopropanol, butanol, isobutanol, sec-butanol, tert-butanol, pentanol, isopentanol, sec-pentanol, tert-pentanol, neopentanol, hexanol, heptanol, octanol, 2-ethylhexanol, nonanol, isononanol, decanol, undecanol, dodecanol, tridecanol, isotridecanol, tetradecanol, pentadecanol, hexadecanol, heptadecanol, octadecanol, eicosanol, cyclopentanol, cyclohexanol, cycloheptanol, cyclooctanol, benzyl alcohol, 2-phenylethanol, 3-phenylpropanol and 4-phenylbutanol. It is also possible to use mixtures of the abovementioned alcohols. Very particular preference is given to $C_1$- to $C_8$-alkanols.

The hydroxyl-containing organic compounds are used in stoichiometric amounts or in excess, based on the ethylenically unsaturated double bond equivalents of the olefin, and also as solvent. If the hydroxyl-containing compounds also react with additional functional groups in the olefins, the amount of hydroxyl-containing compounds has to be increased accordingly.

The olefin used can be any organic compound which contains at least one ethylenically unsaturated double bond.

It may be aliphatic, aromatic or cycloaliphatic and may consist of a linear or branched structure. The olefin is preferably of from 2 to 30 carbon atoms. More than one ethylenically unsaturated double bond may be present, for example in dienes or trienes. The olefin may additionally contain functional groups, such as halogen atoms, carboxyl groups, carboxylic ester functions, hydroxyl groups, ether bridges, sulfide bridges, carbonyl functions, cyano groups, nitro groups or amino groups.

Typical examples of such olefins are ethylene, propene, 1-butene, cis- and trans-2-butene, 1,3-butadiene, pentenes, isoprene, hexenes, octenes, nonenes, decenes, undecenes, dodecenes, cyclopentene, cyclohexene, dicyclopentadiene, methylenecyclopropane, vinylcyclohexane, vinylcyclohexene, allyl chloride, acrylic acid, methacrylic acid, crotonic acid, vinylacetic acid, allyl alcohol, alkyl acrylates, alkyl methacrylates, oleic acid, linoleic acid, linolenic acid, esters and glycerides of such unsaturated fatty acids, styrene, α-methylstyrene, divinylbenzene, indene and stilbene. Mixtures of the stated olefins may also be used in the process of the present invention.

The process of the present invention is particularly suitable for preparing glycol monoethers from linear or branched $C_2$- to $C_5$-alkenes, in particular propene.

The glycol monoethers produced by the process of the present invention contain the structural units

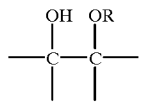

where R is the residue of the hydroxyl-containing organic compound used. The glycol monoethers are frequently isomeric mixtures in which the OH group and the OR group are interchanged.

The reaction conditions for the process of the present invention with respect to temperature, pressure, mode of addition of the starting materials and the reaction time vary depending on the structures of the starting materials. As a rule, the reactivity of the system decreases with increasing chain length or increasing molecule size of olefins used and hydroxyl-containing organic compounds used, thus necessitating more severe reaction conditions.

Typical reaction conditions for the reaction of linear or branched $C_2$- to $C_5$-alkenes, which are mostly gaseous under standard conditions, with aqueous $H_2O_2$ in the presence of $C_1$- to $C_8$-alkanols, which are usually present in excess, are as follows: temperature from $-30°$ C. to $+80°$ C., in particular from $-10°$ C. to $+50°$ C., under autogeneous pressure at reaction temperature, reaction time from 1 to 10 hours.

The process of the present invention can be carried out on a laboratory scale and on an industrial scale, in batchwise or continuous operation. The reactants can be contacted with the catalyst mixture in both a slurry and a fixed bed procedure. The reaction may be carried out in the gas phase, liquid phase or supercritical phase, preference being given to the liquid phase.

A further advantage is that the use of heterogeneous epoxidation and alkoxylation catalysts allows regeneration of deactivated catalysts by washing with the alcohol to be used in the reaction or thermally under oxidizing conditions.

In many cases, the process of the present invention provides for virtually complete conversion of the olefins to the glycol monoethers. If substantial amounts of epoxide intermediates are still present in the final product, these can usually be completely removed by simple methods, for example by distillation or gas expulsion (in the case of volatile epoxides such as propylene oxide).

The examples which follow illustrate the invention without restricting it. The preparation conditions, conversions and yields were not optimized.

EXAMPLES

Example 1

Preparation of an Epoxidation Catalyst 455 g of tetraethyl orthosilicate were placed in a 2 l four-necked flask and 15 g of tetraisopropyl orthotitanate were added in the course of 30 minutes from a dropping funnel while stirring (250 rpm, paddle stirrer). A colorless, clear mixture formed. Finally, 800 g of a 20% strength by weight tetrapropylammonium hydroxide solution (alkali metal content <10 ppm) were added and stirring was continued for a further hour. The alcohol mixture (about 450 g) formed by hydrolysis was distilled off at from 90° C. to 100° C. After addition of 1.5 l of deionized water, the now slightly opaque sol was transferred to a stirred 2.5 l stainless steel autoclave.

The closed autoclave (anchor stirrer, 200 rpm) was brought to a reaction temperature of 175° C. at a heating rate of 3° C./min. The reaction was stopped after 92 hours. The cooled reaction mixture (white suspension) was centrifuged and the resulting solid was washed neutral several times with water. The solid obtained was dried at 110° C. in the course of 24 hours (weight obtained 149 g). Finally, the template still present in the zeolite was burnt off in air at 550° C. in the course of 5 hours (loss on calcination: 14% by weight).

The pure white product had a titanium content of 1.5% by weight and a residual alkali metal content of less than 100 ppm, according to wet chemical analysis. The yield based on $SiO_2$ used was 97%. The crystallite size was about 0.05–0.25 μm and the product showed a typical infrared band at about 960 cm$^{-1}$.

Example 2

Preparation of an Alkoxylation Catalyst 60.0 g of boric acid were dissolved in a solution of 343.8 g of tetraethylammonium hydroxide (40% by weight in water) and 206.2 g of deionized water in a beaker. This solution was transferred into a stirred 2.5 l stainless steel autoclave. 550.0 g of colloidal silica sol (Ludox® AS40) were added to this mixture with stirring.

The mixture was crystallized at 150° C. over the course of 216 hours, separated off, washed with deionized water and dried at 120° C. for 24 hours. The weight obtained was 279 g. Finally, the product was calcined at 500° C. in air over the course of 5 hours to give the H-B-β-zeolite.

Example 3

Single-Stage Preparation of a Glycol Monoether from Propene and Methanol 45 ml of methanol, 1.5 g of titanium silicalite powder from Example 1 and 1.5 g of zeolite H-ZSM-5 were placed in a 250 ml glass autoclave and the suspension was stirred using a magnetic stirrer. The closed glass autoclave was then cooled to $-30°$ C. and pressurized with 20.7 g of propene. The glass autoclave was then warmed to 0° C. and 30 g of a 30% strength by weight hydrogen peroxide solution were metered in. The reaction mixture was stirred at 0° C. under autogeneous pressure for 5 h. The catalyst was then removed by centrifugation and the solution was analyzed by gas chromatography. The solution contained 9.7% by weight of propylene oxide and 8.2% by weight of methoxypropanols.

Example 4
Single-Stage Preparation of a Glycol Monoether from Propene and Ethanol 45 ml of ethanol, 1.5 g of titanium silicalite powder from Example 1 and 1.5 g of zeolite H-ZSM-5 were placed in a 250 ml glass autoclave and the suspension was stirred using a magnetic stirrer. The closed glass autoclave was then cooled to -30° C. and pressurized with 20.7 g of propene. The glass autoclave was then warmed to 0° C. and 30 g of a 30% strength by weight hydrogen peroxide solution were metered in. The reaction mixture was stirred at 0°C. under autogeneous pressure for 5 h. The catalyst was then removed by centrifugation and the solution was analyzed by gas chromatography. The solution contained 4.5% by weight of propylene oxide and 2.2% by weight of ethoxypropanols.

Example 5
Single-Stage Preparation of a Glycol Monoether from Propene and Butanol 45 ml of butanol, 1.5 ml of titanium silicalite powder from Example 1 and 1.5 g of H-B-β-zeolite were placed in a 250 ml glass autoclave and the suspension was stirred using a magnetic stirrer. The closed glass autoclave was then cooled to -30° C. and pressurized with 20.7 g of propene. The glass autoclave was then warmed to 0° C. and 30 g of a 30% strength by weight hydrogen peroxide solution were metered in. The reaction mixture was stirred at 0° C. under autogeneous pressure for 5 h. The catalyst was then removed by centrifugation and the solution was analyzed by gas chromatography. The solution contained 0.3% by weight of propylene oxide and 3.8% by weight of butoxypropanols.

Example 6
Single-Stage Preparation of a Glycol Monoether from Propene and Ethanol 45 ml of ethanol, 1.5 ml of titanium silicalite powder from Example 1 and 1.5 g of polymeric, acidic cation exchanger (Lewatit®, from Bayer) were placed in a 250 ml glass autoclave and the suspension was stirred using a magnetic stirrer. The closed glass autoclave was then cooled to -30° C. and pressurized with 20.7 g of propene. The glass autoclave was then warmed to 0° C. and 30 g of a 30% strength by weight hydrogen peroxide solution were metered in. The reaction mixture was stirred at 0° C. under autogeneous pressure for 5 h. The catalyst was then removed by centrifugation and the solution was analyzed by gas chromatography. The solution contained 4.5% by weight of propylene oxide and 2.2% by weight of ethoxypropanols.

Comparative Example A
Single-Stage Preparation of a Glycol Monoether from Propene and Methanol 45 ml of methanol and 1.5 g of titanium silicalite powder from Example 1 were placed in a 250 ml glass autoclave and the suspension was stirred using a magnetic stirrer. The closed glass autoclave was then cooled to -30°C. and pressurized with 5.8 g of propene. The glass autoclave was then warmed to 0° C. and 32 g of a 30% strength by weight hydrogen peroxide solution were metered in. The reaction mixture was stirred at 0° C. under autogeneous pressure for 2 h. The catalyst was then removed by centrifugation and the solution was analyzed by gas chromatography. The solution contained 8.65% by weight of propylene oxide, 0.04% by weight of methoxy-2-propanol and 0.09% by weight of methoxy-3-propanol.

What is claimed is:

1. A process for preparing glycol monoethers from olefins, which comprises reacting the olefins with an epoxidizing reagent in the simultaneous presence of hydroxyl-containing organic compounds over a mixture of epoxidation catalysts and solid alkoxylation catalysts, wherein said epoxidation catalysts are titanium-containing silicates or titanium-, vanadium-, germanium- or tin-containing zeolites.

2. A process as claimed in claim 1, wherein the solid alkoxylation catalyst used in the catalyst mixture are mineral acid acidic catalysts, solid acidic heterogeneous catalysts, or solid basic catalysts.

3. A process as claimed in claim 2, wherein the solid acidic alkoxylation catalysts are supported mineral acid solid heterogeneous catalysts, polymeric acidic ion exchange resins, composites of acidic ion exchange resins in inorganic materials, acid metal oxides or acidic zeolites.

4. A process as claimed in claim 2, wherein the solid basic alkoxylation catalysts are alkali metal or alkaline earth metal oxide or hydroxide solid basic catalysts, supported bases, polymeric basic ion exchange resins, dendrimeric amines, talcites or hydrotalcites.

5. A process as claimed in claim 1, wherein the epoxidizing reagent used is aqueous hydrogen peroxide or a hydrogen/oxygen mixture.

6. A process as claimed in claim 1, wherein the hydroxyl-containing organic compounds used are linear or branched $C_1$- to $C_{20}$-alkanols, $C_5$- to $C_8$-cycloalkanols or $C_7$- to $C_{20}$-arylalkanols.

7. A process as claimed in claim 1, wherein the olefins used are those having from 2 to 30 carbon atoms and one or more ethylenically unsaturated double bonds.

8. A process as claimed in claim 7, wherein the olefins used are linear or branched $C_2$- to $C_5$- alkene.

9. The process of claim 1, wherein said epoxidation catalysts are titanium or vanadium silicalites having a zeolite structure assigned by X-ray diffraction to the MFI, MEL, BEA, MTW, TON, FER or FMI/MEL mixed structure.

10. The process of claim 8, wherein said olefin is propene.

\* \* \* \* \*